United States Patent
Murray et al.

(10) Patent No.: US 7,671,195 B2
(45) Date of Patent: Mar. 2, 2010

(54) PROCESS FOR PREPARING DIBENZOTHIAZEPINE COMPOUNDS

(75) Inventors: Paul Michael Murray, Loughborough (GB); Luis-Manuel Vaz, Loughborough (GB); Debra Ainge, Loughborough (GB); Katsumasa Harada, Ube (JP); Shigeyoshi Nishino, Ube (JP); Kiyotaka Yoshii, Ube (JP)

(73) Assignees: AstraZeneca UK Limited, London (GB); UBE Industries, Ltd., Ube-Shi, Yamaguchi (JP)

( * ) Notice: Subject to any disclaimer, the term of this patent is extended or adjusted under 35 U.S.C. 154(b) by 290 days.

(21) Appl. No.: 11/708,704

(22) Filed: Feb. 21, 2007

(65) Prior Publication Data
US 2007/0203336 A1    Aug. 30, 2007

Related U.S. Application Data

(60) Provisional application No. 60/775,483, filed on Feb. 22, 2006.

(51) Int. Cl.
*C07D 281/18* (2006.01)
(52) U.S. Cl. .................................... 540/488
(58) Field of Classification Search ................. 540/488
See application file for complete search history.

(56) References Cited

U.S. PATENT DOCUMENTS 7,314,930 B2    1/2008    Harada et al.

FOREIGN PATENT DOCUMENTS

EP    1 201 663    5/2002
WO    WO 2004 047722    6/2004
WO    WO 2005 012274    2/2005

OTHER PUBLICATIONS

Jaques R., et al., "Dibenzothiazepine Derivatives and the Pharmacological Effect thereof," Helv. Chim. Acta., vol. 42, No. 134, pp. 1265-1278, Fasiculus IV (Apr. 25, 1959).—*English language translation* (pp. 1-19) of XP-00 244 910.8.

Jaques R., et al., *Über Dibenzo-thiazepin-Derivate und ihre pharmakoligische Wirkung*, Helv. Chim. Acta, vol. 42, No. 134, pp. 1265-1278 (1959).

Zirnis, A. et al., The Synthesis of Possible Hydroxylated Metabolics of 2-Chlorophenothiazine Derivatives (1), J. Heterocycl. Chem., vol. 14, pp. 107-112 (Feb. 1977).

William S. Johnson and Robert D. Offenhauer, *4-(p-Hydroxyphenyl)-hexahydroacetophenone and Homologs*, J. Amer. Chem. Soc., vol. 67, No. 7, pp. 1045-1049 (Jul. 10, 1945).

International Search Report Application PCT/JP2007/053700 dated Nov. 13, 2007.

*Primary Examiner*—Bruck Kifle
(74) *Attorney, Agent, or Firm*—Nixon Peabody, LLP; Jeffrey L. Costellia

(57) ABSTRACT

A dibenzothiazepine compound is suitably prepared by subjecting a 2-amino-2'-carboxy-diphenylsulfide compound to dehydration-condensation reaction in the presence of an acidic catalyst; the 2-amino-2'-carboxy-diphenylsulfide compound is suitably prepared by reducing a 2-nitro-2'-carboxy-diphenylsulfide compound in a lower aliphatic ester solvent; and the 2-nitro-2'-carboxy-diphenylsulfide compound is suitably prepared by reacting a nitrobenzene compound with a thiosalicylic acid compound in a mixture of a lower aliphatic alcohol and water.

17 Claims, No Drawings

PROCESS FOR PREPARING DIBENZOTHIAZEPINE COMPOUNDS

This application claims priority of U.S. Application No. 60/775,483 filed Feb. 22, 2006, now pending.

FIELD OF THE INVENTION

The present invention is directed, in part, to methods of preparing a dibenzothiazepine derivative. In particular, the invention relates to methods for preparing a dibenzothiazepine derivative which can be used as an intermediate compound for preparing 11-[4-(2-(2-hydroxyethoxy)ethyl]-1-piperadinyl-dibenzothiazepine and its derivatives, which is known to be effective as an antipsychotic pharmaceutical.

BACKGROUND OF THE INVENTION

EP 0282236-A1 reports that a dibenzothiazepine derivative can be processed to give 11-[4-(2-(2-hydroxyethoxy)-ethyl]-1-piperadinyldibenzothiazepine derivative, which is of value as, for example, an antipsychotic pharmaceutical. In more detail, dibenzo-[b,f][1,4]thiazepin-11-one, which is a representative compound of the dibenzothiazepine derivatives reported therein, is reacted with phosphorus oxychloride to yield a 11-chloro-dibenzothiazepine derivative. To the 11-chloro-dibenzothiazepine derivative is added piperazine to yield a 11-piperazinyl-dibenzothiazepine derivative, which is subsequently reacted with 2-chloroethoxyethanol under basic conditions to give the desired 11-[4-(2-(2-hydroxyethoxy)-ethyl]-1-piperadinyldibenzothiazepin.

EP 0282236-A1 further reports that the dibenzo-[b,f][1,4]thiazepin-11-one is prepared from phenyl 2-(phenylthio)phenylcarbamate or its analogous compound by cyclization in the presence of polyphosphoric acid.

Helv. Chim. Acta., 1959, 42, 1263 reports that a dibenzothiazepine derivative can be prepared by heating a methyl thiosalicylate derivative with a 2-halogenated nitro-benzene derivative in the presence of sodium to give a 2-nitro-2'-carboxy-diphenylsulfide derivative, which is then reduced using a Raney-nickel catalyst to yield a 2-amino-2'-carboxy-diphenylsulfide derivative, which is finally heated to give a dibenzothiazepine derivative.

Org. Prep. Proced. Int., 1974, 287 reports that a dibenzothiazepine derivative can be prepared by heating a thiosalicylic acid ester derivative and 2-iodo-nitrobenzene derivative in the presence of sodium methylate and copper, treating the resulting compound successively with an alkaline solution and an acidic solution to give a 2-nitro-2'-carboxy-diphenylsulfide derivative, reducing the derivative by ferrous sulfate in an aqueous ammonia solution to give a 2-amino-2'-carboxy-diphenylsulfide derivative, and heating the resulting derivative under reduced pressure.

WO 92/19607 reports that a dibenzothiazepine derivative can be prepared by the steps of reacting 2-amino-thiophenol with 2-fluorobenzonitrile to give 2-(2-amino-phenylthio)benzonitrile, hydrolyzing the resultant compound to give 2-(2-carboxyphenylthio)aniline, and finally cyclizing the aniline derivative.

As described above, various processes for preparing a dibenzothiazepine derivatives are known. However, the known processes have various disadvantageous features such as a low yield, high temperature reaction conditions, use of starting compounds which are not easily available, and/or complicated post-treatment. These disadvantageous features are naturally unfavorable in the industrial preparation of the desired dibenzothiazepine derivative.

EP 1201663A1 and WO 2004/047722 A2 also report preparation of dibenzothiazepine derivatives.

SUMMARY OF THE INVENTION

The present invention provides methods of preparing dibenzothiazepine compounds in good yield without complicated post treatment, employing easily available materials such as, for example, a nitrobenzene compound and thiosalicylic acid compound. Each of the compounds and methods, and steps thereof, are useful in, for example, the preparation of pharmaceuticals such as, for example, quetiapine. The present invention also provides, inter alia, improved isolation of the nitro acid compound as well as improved quality of the isolated lactam compound.

The invention resides, in part, in a method of preparing a dibenzothiazepine compound of Formula I:

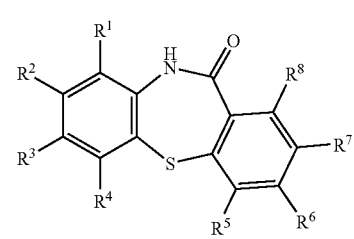

(I)

in which each of $R^1$, $R^2$, $R^3$, $R^4$, $R^5$, $R^6$, $R^7$ and $R^8$, independently, represents a hydrogen atom, an alkyl group, an alkoxy group, an alkylcarbonyl group, an aryl group, an aryloxy group, or an arylcarbonyl group, each group being optionally substituted, which comprises a step of subjecting a 2-amino-2'-carboxy-diphenylsulfide compound of Formula V:

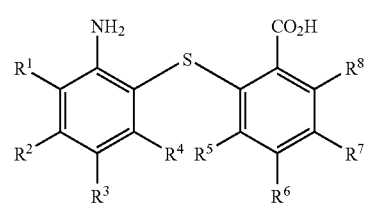

(V)

in which each of $R^1$, $R^2$, $R^3$, $R^4$, $R^5$, $R^6$, $R^7$ and $R^8$ is the same as defined above, to dehydration-condensation reaction in the presence of an acidic catalyst.

The 2-amino-2'-carboxy-diphenylsulfide of Formula V can be prepared by a known method. However, the 2-amino-2'-carboxy-diphenylsulfide may be suitably prepared by the below-described method.

The invention further resides, in part, in a method of preparing a 2-amino-2'-carboxy-diphenylsulfide compound of the above-mentioned Formula V, which comprises a step of reducing a 2-nitro-2'-carboxy-diphenylsulfide compound of Formula IV:

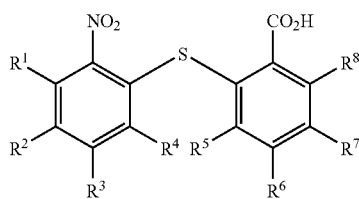

in which each of $R^1$, $R^2$, $R^3$, $R^4$, $R^5$, $R^6$, $R^7$ and $R^8$ is the same as defined above, in an aliphatic ester of an aliphatic alcohol having 1 to 6 carbon atoms and an aliphatic carboxylic acid having 1 to 6 carbon atoms.

The 2-nitro-2'-carboxy-diphenylsulfide compound of Formula IV can be prepared by a known method. However, the 2-nitro-2'-carboxy-diphenylsulfide compound is suitably prepared by the below-described method.

The invention further resides, in part, in a method of preparing 2-nitro-2'-carboxy-diphenylsulfide compound of the above-mentioned Formula IV, which comprises a step of reacting a nitrobenzene compound of Formula II:

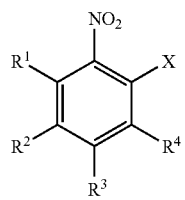

in which each of $R^1$, $R^2$, $R^3$, and $R^4$ is the same as defined above, with a thiosalicylic acid compound of Formula III:

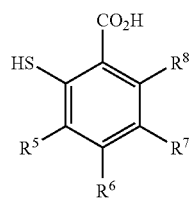

in which each of $R^5$, $R^6$, $R^7$ and $R^8$ is the same as defined above, in a mixture of an aliphatic alcohol having 1 to 6 carbon atoms and water.

The method of preparing dibenzothiazepine compounds of Formula I according to the invention is illustrated by Scheme 1:

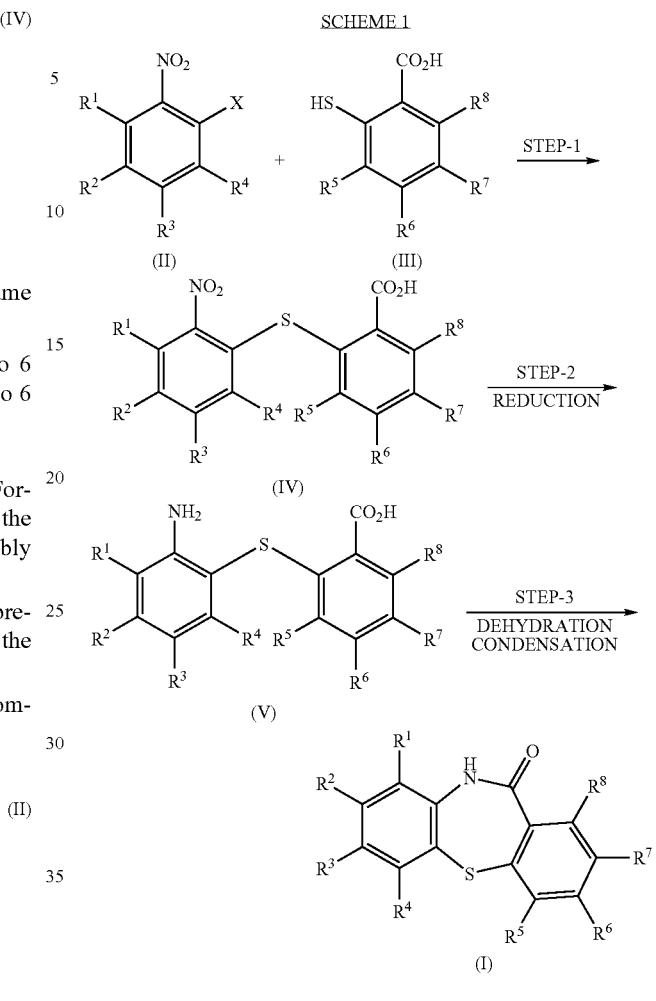

DESCRIPTION OF EMBODIMENTS

In the formulas of the compounds involved in the methods described herein, an "alkyl group" means a straight chain or branched chain alkyl group of 1 to 10 carbon atoms, or 1 to 8 carbon atoms, or 1 to 6 carbon atoms, or 1 to 5 carbon atoms having no substituent, or a straight chain or branched chain alkyl group of 1 to 10 carbon atoms, or 1 to 8 carbon atoms, or 1 to 6 carbon atoms, or 1 to 5 carbon atoms comprising one or more substituents. Examples of alkyl groups include, but are not limited to, methyl, ethyl, propyl, butyl, pentyl, hexyl, heptyl, octyl, nonyl, and decyl, and including all isomers of each of the foregoing, and all subgroups thereof. Suitable alkyl groups are methyl, ethyl, propyl, butyl, pentyl, hexyl, heptyl, and octyl. Also suitable are methyl, ethyl, propyl, butyl, and pentyl.

The substituent of the above-mentioned straight chain or branched chain alkyl group comprising one or more substituents can be attached to any position of the alkyl moiety. Examples of the substituents include, but are not limited to, straight chain or branched chain alkoxy groups comprising 1 to 10 carbon atoms such as methoxy, ethoxy, propoxy, butoxy, pentyloxy, hexyloxy, heptyloxy, octyloxy, nonyloxy, and decyloxy, and including all isomers of each of the foregoing, and all subgroups thereof; alkylcarbonyl groups comprising 2 to 6 carbon atoms and contain a straight chain or branched chain alkyl group comprising 1 to 5 carbon atoms, such as acetyl, propionyl, butanoyl, and pentanoyl, and including all isomers of each of the foregoing, and all subgroups thereof; phenylcarbonyl groups which may comprise one or more substituents; and phenyl which may comprise one or more substituents.

As used herein, a "phenylcarbonyl group" means a phenylcarbonyl group comprising no substituent or phenyl-carbonyl group comprising one or more substituents. As used herein, a "phenyl group" means phenyl group comprising no substituent or phenyl group comprising one or more substituents. The substituent for the phenylcarbonyl group and phenyl group can be phenyl, phenylcarbonyl, or one of the above-mentioned alkyl, alkoxy, and alkylcarbonyl groups.

As used herein, an "alkoxy group" means an alkoxy group comprising 1 to 10 carbon atoms and containing a straight chain or branched chain alkyl moiety which comprises no substituent and comprises 1 to 10 carbon atoms, or an alkoxy group having 1 to 10 carbon atoms and containing a straight chain or branched chain alkyl moiety which comprises one or more substituents and comprises 1 to 10 carbon atoms. Examples of an "alkoxy group" include, but are not limited to, the above-mentioned alkyl groups, an alkylcarbonyl group comprising 2 to 6 carbon atoms, a phenylcarbonyl group which can comprise one or more substituents and a phenyl which can comprise one or more substituents.

An "alkylcarbonyl group" means an alkylcarbonyl group comprising 2 to 11 carbon atoms and containing a straight chain or branched chain alkyl moiety which comprises no substituent and comprises 1 to 10 carbon atoms, or an alkylcarbonyl group comprising 2 to 11 carbon atoms and containing a straight chain or branched chain alkyl moiety which comprises one or more substituents and comprises 1 to 10 carbon atoms. Examples of the alkyl moieties of "alkyl-carbonyl group" include, but are not limited to, those described above.

An "aryl group" means an aryl group comprising no substituent or an aryl group comprising one or more substituents. Examples of "aryl groups" include, but are not limited to, phenyl, naphthyl, and anthoryl, and any subset thereof. Suitable groups are phenyl and naphthyl. A suitable group is phenyl. Examples of substituents of the "aryl group" include, but are not limited to, those described above for the alkyl groups.

An "aryloxy group" means an aryloxy group comprising an aryl moiety comprising no substituent or an aryloxy group comprising an aryl moiety comprising one or more substituents. Examples of aryl groups of an "aryloxy group" include, but are not limited to, substituents described above for the alkyl group.

An "arylcarbonyl group" means an arylcarbonyl group comprising an aryl moiety comprising no substituent, or an arylcarbonyl group comprising an aryl moiety comprising one or more substituents. Examples of aryl groups of an "arylcarbonyl group" include, but are not limited to, the substituents described above for the alkyl group.

The groups of $R^1$ through $R^8$ may be the same or different from each other, and each can be a hydrogen atom, an alkyl group, an alkoxy group, an alkylcarbonyl group, an aryl group, an aryloxy group, or an arylcarbonyl group. Also suitable are a hydrogen atom, an alkyl group, an alkoxy group, and an alkylcarbonyl group.

The halogen atom for X of Formula II can be fluorine, chlorine, bromine, or iodine. Also suitable are fluorine, chlorine, and bromine. Also suitable is chlorine.

Each of the steps of the method for preparing the dibenzothiazepine compounds according to the invention is described hereinafter in more detail.

In the first step of the method for preparing the dibenzothiazepine compounds of the invention, a nitrobenzene compound of Formula II and a thiosalicylic acid compound of Formula III are reacted in a solvent, in the presence of a base, to prepare a 2-nitro-2'-carboxy-diphenylsulfide compound of Formula IV.

Examples of the nitrobenzene compounds of Formula II employed in the first step include, but are not limited to, 2-chloronitrobenzene, 2-bromonitrobenzene, 2-fluoronitrobenzene, 2-iodonitrobenzene, 2-chloro-5-methoxynitrobenzene, 2-bromo-5-methoxynitrobenzene, 2-fluoro-5-methoxynitrobenzene, 2-iodo-5-methoxynitrobenzene, 2-chloro-5-methylnitrobenzene, 2-bromo-5-methylnitrobenzene, 2-fluoro-5-methylnitrobenzene, 2-iodo-5-methylnitrobenzene, 2-chloro-5-phenylnitrobenzene, 2-bromo-5-phenylnitrobenzene, 2-fluoro-5-phenylnitrobenzene, 2-iodo-5-phenylnitrobenzene, 2-chloro-5-acetylnitrobenzene, 2-bromo-5-acetylnitrobenzene, 2-fluoro-5-acetylnitrobenzene, and 2-iodo-5-acetylnitrobenzene, or any subgroup thereof. Suitable are 2-halonitrobenzenes such as, for example, 2-chloronitrobenzene and 2-bromonitrobenzene. Also suitable is 2-chloronitrobenzene.

Examples of the thiosalicylic acid compounds of Formula III employed in the first step include, but are not limited to, thiosalicylic acid, 5-methoxy-thiosalicylic acid, 5-methylthiosalicylic acid, 5-phenyl-thiosalicylic acid, and 5-acetyl-thiosalicylic acid, or any subgroup thereof. Suitable are thiosalicylic acid and 5-methoxythiosalicylic acid. Also suitable is thiosalicylic acid.

The nitrobenzene compound of Formula II is generally employed in an amount of 0.7 to 10 mol., or 1.0 to 5 mol., per one mol. of the thiosalicylic acid of Formula III. In some embodiments, 1.0 to 1.32, or 1.1 to 1.32, or 1.2 to 1.32 eq 2-chloronitrobenzene is used.

The above-mentioned first step is generally performed in a solvent. There are no specific limitations on the solvents, so long as the solvents do not participate in the reaction. Examples of the solvents include, but are not limited to, water; amide solvents such as N,N-dimethyl-formamide, N,N-dimethylacetamide, N-methylpyrrolidone and dimethylimidazolidone; aliphatic alcohols such as methanol, ethanol, n-propanol, isopropanol, n-butanol, and 1-pentanol; ketones such as acetone, methyl ethyl ketone and methyl isobutyl ketone; nitriles such as acetonitrile and benzonitrile; or any combination thereof. Suitable are water, amides and aliphatic alcohols. More suitable are mixtures of lower aliphatic alcohols (i.e., aliphatic alcohols having 1 to 6 carbon atoms) and water. The mixture suitably comprises the lower aliphatic alcohol and water in a volume ratio of 10/1 to 1/10 (also suitably 5/1 to 1/10) in terms of the former to the latter. In the mixture, the lower aliphatic alcohol also suitable is isopropyl alcohol.

In some embodiments, the nitrobenzene compound of Formula II, such as 2-chloronitrobenzene, and the thiosalicylic acid compound of Formula III, such as thiosalicylic acid, are charged to a reactor at 20-25° C., followed by isopropanol and water. The reactor containing the nitrobenzene compound of Formula II and the thiosalicylic acid compound of Formula III can be inerted with, for example, nitrogen.

The solvent in the first step can be employed in such manner that a weight ratio of the amount of the thiosalicylic acid against the amount of the solvent (such as a water/isopropyl alcohol mix) is in the range of 0.08 to 0.31, 0.12 to 0.27, or 0.16 to 0.23.

The reaction of the first step is generally performed in the presence of a base. Examples of the suitable bases include, but are not limited to, potassium carbonate, sodium carbonate, lithium carbonate, sodium hydroxide, potassium hydroxide, lithium hydroxide, and sodium methylate, or any subgroup thereof. Also suitable are potassium carbonate, sodium carbonate, sodium hydroxide, potassium hydroxide, and sodium methylate, or any subgroup thereof. The base is generally employed in an amount corresponding to 1 to 10 moles, or 1.5 to 5 moles, or 2.0 to 2.3 moles, or 2.1 to 2.27 moles per one mole of the total amounts of the starting compounds.

The reaction of the first step is generally performed at a temperature of not higher than the boiling temperature of the solvent employed, such as at a temperature of 0 to 150° C., or 20 to 100° C., or 70 to 84° C., or 79 to 84° C. The reaction period of the first step greatly depends on the reaction temperature, but the reaction is generally complete within 20 hours. In some embodiments, the reaction mixture is heated to reflux (about 84° C.) and is held at this temperature for 6 hours.

In the reaction of the first step, additives for accelerating the reaction other than the base can be added. Examples of the additives include, but are not limited to, potassium iodide and N,N-dimethylaminopyridine. The additive can be employed in an amount of 0.0005 to 0.5 mol. (mol of additive/mol of nitrobenzene compound), or 0.001 to 0.1 mol., per one mole of the nitrobenzene compound of Formula II.

The chemical structure of the 2-nitro-2'-carboxydiphenylsulfide compound of Formula IV obtained in the first step of the invention depends on the chemical structure of the nitrobenzene compound of Formula II as well as on the chemical structure of the thiosalicylic acid compound of Formula III. Examples of 2-nitro-2'-carboxydiphenylsulfide derivatives include, but are not limited to, 2-nitro-2'-carboxydiphenylsulfide, 2-nitro-4-methoxy-2'-carboxydiphenylsulfide, 2-nitro-4-methyl-2'-carboxydiphenylsulfide, 2-nitro-4-phenyl-2'-carboxydiphenylsulfide, 2-nitro-4-acetyl-2'-carboxydiphenylsulfide, and 2-nitro-2'-carboxy-4'-methoxydiphenylsulfide, or any subgroup thereof. Also suitable are 2-nitro-2'-carboxydiphenylsulfide and 2-nitro-2'-carboxy-4'-methoxydiphenylsulfide.

The 2-nitro-2'-carboxydiphenylsulfide compound of Formula IV prepared in the first step can be recovered by a combination of a conventional washing procedure and a conventional separating procedure, such as a combination of addition of an acid to make the reaction mixture acidic and filtration of the precipitated crystalline product to obtain a crude product, or a combination of addition of water and an extracting solvent (organic solvent) to the reaction mixture and addition of an acid to make the aqueous phase of the reaction mixture acidic. Otherwise, the crude product can be recovered by placing the organic solvent portion under reduced pressure. Thus, obtained crude product per se can be employed in the next step. The crude product can be further purified, if necessary, by column or recrystallization. The process for purification can be selected depending on each compound to be purified. The acid employed can be hydrochloric acid, sulfuric acid, phosphoric acid, or acetic acid, or any subgroup thereof.

In the second step of the process of the invention, the 2-nitro-2'-carboxydiphenylsulfide compound of Formula IV is reduced to give a 2-amino-2'-carboxydiphenylsulfide compound of Formula V.

The reduction procedure performed in the second step is not limited, and known procedures for reducing the nitro group can be employed. Suitable procedures include, for example, the Raney-nickel method (hereinafter, referred to as "Reaction A"), the ferrous salt method (hereinafter, referred to as "Reaction B") and a method employing palladium, platinum or its compounds (hereinafter, referred to as "Reaction C"). In reduction procedure, hydrogen gas is employed as supply source of hydrogen.

Reaction A: Raney-nickel Method

Raney-nickel can be employed in the method in an amount of 1.0 to 80 wt. % (in terms of nickel), or 5.0 to 40 wt. %, per the amount of the 2-nitro-2'-arboxydiphenylsulfide compound of Formula IV. Examples of Raney-nickels employable in the reaction include, but are not limited to, 10-60% Ni—Al alloy and that containing Cr and Mo. Stabilized can be also employed. The yield is not greatly influenced by the developing method of Raney-nickel. In the case of using the Raney-nickel method, the reaction is generally performed in the presence of hydrogen gas under pressure. Accordingly, the reaction is generally performed in an autoclave. The hydrogen gas pressure can be as high as possible. Generally, the hydrogen gas pressure is in the range of 5 to 100 barg. The reaction may be performed under atmospheric pressure. In this case, the reaction is carried out in the stream of hydrogen gas.

There are no specific limitations on the solvents employed in Reaction A, so long as the solvents do not participate in the reaction. Examples of the solvents include, but are not limited to, aliphatic alcohols such as methanol, ethanol, n-propanol, isopropanol and n-butanol. The volume of the solvent is so selected that the volume of 2-nitro-2'-carboxy-diphenylsulfide compound of Formula IV would be 0.05 to 0.6 volume, or 0.1 to 0.6 volume per one volume of the solvent (volume of 2-nitro-2'-carboxydiphenylsulfide compound of the formula/volume of solvent).

Reaction A can be carried out at a temperature up to the boiling point of the solvent. The reaction is generally carried out at a temperature of 20 to 200° C., or 25 to 150° C. The reaction period depends on the temperature and hydrogen gas pressure. The reaction is usually complete within 20 hours.

After Reaction A is complete, the 2-amino-2'-carboxydiphenylsulfide compound of Formula V produced in the reduction can be recovered by a conventional combination of a washing procedure and a separating procedure, such as a combination of filtration of the reaction mixture and concentration of the filtrate under reduced pressure. The product obtained above per se can be employed in the next step. If desired, the product can be purified by column chromatography or recrystallization. The purification procedure can be selected depending on the product to be purified.

Reaction B: Ferrous Salt Method

Examples of ferrous salts employable in the reaction include, but are not limited to, ferrous sulfate and ferrous chloride. These salts can be employed in the form of hydrate or anhydride. Suitable are ferrous sulfate 7 hydrates, ferrous salt anhydrides, ferrous salt 4 hydrates, and ferrous salt n hydrates. The salt can be employed in a volume of 0.1 to 30 (in terms of iron atom), or 0.5 to 10, per one volume of the 2-nitro-2'-carboxydiphenylsulfide of Formula IV.

Mixture of water and aqueous ammonia is generally employed as a solvent for Reaction B. Aqueous ammonia can be prepared by employing concentrated aqueous ammonia (ammonia concentration: 25 to 28 wt. %). Aqueous ammonia of lower concentration or water containing ammonia gas can be also employed, so long as the content of ammonia is sufficient. Water can be so employed that the volume of 2-nitro-2'-carboxydiphenylsulfide derivative of Formula IV would be 0.01 to 0.4 equivalent per one volume of water (volume of 2-nitro-2'-carboxy-diphenylsulfide derivative/ volume of water), or 0.02 to 0.2 equivalent (the same as above). The volume of ammonia is selected so that the volume of 2-nitro-2'-carboxydiphenylsulfide derivative would be 0.005 to 0.5 equivalent, or 0.01 to 0.5 equivalent, per one volume of ammonia (volume of 2-nitro-2'-carboxydiphenylsulfide derivative/volume of ammonia).

Reaction B can be carried out at a temperature up to the boiling point of the solvent. The reaction is generally carried out at a temperature of 20 to 100° C., or 40 to 90° C. The reaction period depends on the temperature. The reaction is usually complete within 2 hours.

After Reaction B is complete, the 2-amino-2'-carboxydiphenylsulfide compound of Formula V produced in the reduction can be recovered by a conventional combination of a washing procedure and a separating procedure. For example, the reaction mixture is filtered, and an acid (e.g., hydrochloric acid, sulfuric acid, phosphoric acid and acetic acid) is added to the filtrate, thereby placing its pH on the acidic side. The obtained filtrate is concentrated under reduced pressure to obtain a crude compound. The product obtained above per se can be employed in the next step. If desired, the product can be purified by column chromatography or recrystallization. The purification procedure can be selected depending on the product to be purified.

Reaction C: Method Employing Palladium or Platinum (or Its Compounds)

The reaction can be performed in the presence of a reducing catalyst (i.e., hydrogenation catalyst) selected from the group consisting of palladium (Pd), platinum (Pt), a palladium compound, and a platinum compound, or any combination or subgroup thereof. The reducing catalyst suitably is deposited on a carrier such as carbon (C) or barium sulfate. Suitable are Pt/C, Pd/C, Pd/barium sulfate, Pd—Pt/C (or Pd,Pt/C), and platinum oxide. Also suitable is Pd—Pt/C.

The reducing catalyst comprising palladium or platinum can be employed in an amount corresponding to 0.01 to 30 weight % (in terms of palladium or platinum metal), or 0.05 to 10 weight %, per the amount of the 2-nitro-2'-carboxydisulfide derivative of Formula IV. If the catalyst is deposited on a carrier, the catalyst can be deposited in an amount of 1 to 10 weight % (in terms of palladium or platinum metal), per the amount of the carrier. If Pd/C, Pt/C, or Pd—Pt/C is employed, a dry catalyst having a water content of not more than 5%, as well as a wet catalyst containing water component in a greater amount can be employed. The wet catalyst may contain 10 to 70 weight % (amount of water per the total amount of the catalyst and carrier).

When platinum oxide is employed in Reaction C as the reducing catalyst, it can be employed in an amount of 0.1 to 50 weight %, or 1 to 30 weight %, per the amount of the 2-nitro-2'-carboxydisulfide derivative of Formula IV.

Reaction C is generally performed in the presence of hydrogen gas under pressure. Accordingly, the reaction is generally performed in an autoclave or other reaction vessel. The hydrogen gas pressure can be as high as possible. Generally, the hydrogen gas pressure is in the range of 2 to 100 barg or 4 to 6 barg. The reaction may be performed under atmospheric pressure. In this case, the reduction (or hydrogenation) can be carried out in the stream of hydrogen gas. In some embodiments, hydrogen is introduced into the vessel up to 5 barg and agitation is started and the hydrogen pressure is maintained at 5 barg.

Reaction C is generally carried out in a solvent. There are no specific limitations on the solvent employed, so long as the solvents do not participate in the reaction. Examples of the solvents include, but are not limited to, aliphatic alcohols such as methanol, ethanol, n-propanol, isopropanol and n-butanol, esters such as methyl acetate, ethyl acetate, isopropyl acetate, and n-butyl acetate, and amide solvents such as N,N-dimethylformamide, N,N-dimethyl-acetamide, N-methylpyrrolidone and dimethylimidazolidone, or any combination thereof, or any subgroup thereof. The esters of an aliphatic alcohol having 1 to 6 carbon atoms and an aliphatic carboxylic acid having 1 to 6 carbon atoms are suitable, because the use of the ester solvent can reduce production of by-products (i.e., impurities). The solvent can be employed in an amount of 2 to 70 weight %, or 5 to 50 weight %, per the amount of the 2-nitro-2'-carboxydiphenylsulfide derivative of Formula IV. In some embodiments, a suitable solvent is ethyl acetate.

Reaction C is generally carried out at a temperature of 10 to 200° C., or 20 to 150° C. The reaction period depends on the reaction temperature and hydrogen gas pressure, but generally is not longer than 30 hours. In some embodiments, the reaction suspension is heated to 50° C. and maintained at this temperature and at 5 barg pressure of hydrogen for 5 hours.

The 2-amino-2'-carboxydiphenylsulfide derivative of Formula V produced in Reaction C (hydrogenation) can be recovered by a conventional combination of a washing procedure and a separating procedure, such as a combination of filtration of the reaction mixture and concentration of the filtrate under reduced pressure. The product obtained above per se can be employed in the next step. If desired, the product can be purified by column chromatography or recrystallization. The purifying procedure can be selected dependent on the product to be purified. In some embodiments, at the end of the reaction, the reaction mixture is cooled to 20-25° C. and filtered to remove the catalyst residue. The ethyl acetate solution of amino acid is washed with water. Material can be used directly in the next step without further purification or isolation.

The chemical structure of the 2-amino-2'-carboxydiphenylsulfide compound of Formula V prepared in the second step (reduction step) is dependent on the chemical structure of the 2-nitro-2'-carboxydiphenylsulfide of Formula IV employed in the second step as the starting compound. Examples of 2-amino-2'-carboxydiphenylsulfide compounds of Formula V include, but are not limited to, 2-amino-2'-carboxydiphenylsulfide, 2-amino-4-methoxy-2'-carboxydiphenylsulfide, 2-amino-4-methyl-2'-carboxydiphenylsulfide, 2-amino-4-phenyl-2'-carboxydiphenylsulfide, 2-amino-4-acetyl-2'-carboxydiphenylsulfide, and 2-amino-2'-carboxy-4'-methoxydiphenylsulfide, or any subgroup thereof. Suitable are 2-amino-2'-carboxydiphenylsulfide and 2-amino-2'-carboxy-4'-methoxydiphenylsulfide.

In the third step of the invention, the 2-amino-2'-carboxydiphenylsulfide compound of Formula V is condensed by dehydration to prepare the dibenzothiazepine compound of Formula I.

The reaction of the third step can be performed using no solvent. However, the reaction can be carried out in a hydrophobic organic solvent which does not participate in the reaction. Examples of the organic solvents include, but are not limited to, aromatic hydrocarbons such as toluene, xylene, cumene, and benzene; halogenated aromatic hydrocarbons such as chlorobenzene, 1,2-dichlorobenzene, 1,3-dichlorobenzene, 1,4-dichlorobenzene, bromobenzene, 1,2-dibromobenzene, 1,3-dibromobenzene, and 1,4-dibromobenzene; cyclic aliphatic hydrocarbons such as cyclohexane, cycloheptane, and cyclooctane; and aliphatic esters such as ethyl acetate, butyl acetate, methyl butyrate, ethyl butyrate, and butyl butyrate; or other solvents such as ethanol, 1-pentanol, or methyl isobutylketone; or any combination or subgroup thereof. Suitable are toluene, xylene, cumene, and 1,2-dichlorobenzene.

There is no specific limitation on the amount of the solvent employed in the third step. However, it is suitable that the solvent is employed in an amount to give a ratio of the weight amount of the 2-amino-2'-carboxydiphenylsulfide compound against the volume amount of the solvent (W/V %) of not less than 3%, or in the range of 4 to 40%. The reaction of the third step can be carried out in a Dean-Stark apparatus for performing azeotropic dehydration (for refluxing with removal of water produced in the reaction) so as to accelerate the reaction rate and the conversion ratio. There is no specific limitation on the reaction temperature of the third step. Suitable is a temperature of 100 to 200° C. or 120-140° C. In addition, the reaction of the third step can take place in the presence of an acid catalyst such as, for example, paratoluene sulphonic acid, benzene sulfonic acid, methane sulfonic acid, sulfuric acid, acetic acid, phosphoric acid, hydrochloric acid, nitric acid, or formic acid. The use of an acidic catalyst is effective to accelerate the reaction rate. Other suitable catalysts are para-toluene sulphonic acid, benzene sulfuric acid, methane sulfonic acid, sulfuric acid, and phosphoric acid. Generally, 0.01-20 mol % or 0.05-10 mol % of the acidic catalyst (based on the amount of the amino acid, i.e., 2-amino-2'-carboxydiphenylsulfide compound) is employed. In some embodiments, the amino acid and 0.1-0.2 mol % para-toluene sulphonic acid in xylene are heated at reflux for 10 hours with azeotropic removal of water.

The chemical structure of the dibenzothiazepine compound of Formula I obtained in the third step depends on the chemical structure of the 2-amino-2'-carboxydiphenylsulfide derivative of Formula IV. Examples of the dibenzothiazepine derivatives of Formula I include, but are not limited to, dibenzo[b,f][1,4]thiazepin-11-one, 8-methyl-dibenzo[b,f][1,4]thiazepin-11-one, 8-phenyl-dibenzo[b,f]-[1,4]thiazepin-11-one, 8-methoxy-dibenzo[b,f][1,4]thiazepin-11-one, and 2-methoxy-dibenzo[b,f][1,4]-thiazepin-11-one. Suitable are dibenzo[b,f][1,4]-thiazepin-11-one and 2-methoxy-dibenzo[b,f][1,4]-thiazepin-11-one, or any subgroup thereof.

The dibenzothiazepine compound of Formula I produced in the third step can be easily recovered by cooling the reaction mixture to precipitate a crystalline product of the dibenzothiazepine compound. The precipitated crystalline product is then collected by filtration to give the dibenzothiazepine compound of a high purity. If further purification is required, recrystallization or column chromatography can be utilized. Otherwise, the reaction mixture is made alkaline by addition of an aqueous alkaline solution and then the aqueous portion is removed, in advance of precipitating the resultant product. The remaining organic portion is then cooled to precipitate a crystalline product of the dibenzothiazepine compound. The aqueous alkaline solution can be produced by the use of sodium hydrogen carbonate, sodium carbonate, potassium carbonate, sodium hydroxide, or potassium hydroxide, or any subgroup thereof. The alkaline compound in the alkaline solution can be at a concentration of 0.5 to 30 weight %. There is no limitation on the amount of the alkaline solution, but the alkaline solution can be used in an amount of 0.05 to 0.4 weight part, based on one weight part of the product of the third step (i.e., dibenzothiazepine compound of Formula I). In some embodiments, after heating for ten hours at 140° C., the vessel contents are cooled to 55° C. and the resulting suspension filtered. The dibenzothiazepine lactam filter cake is washed with methanol and dried in vacuo.

Suitable embodiments of the invention are described below.

1) The nitrobenzene compound of Formula II is a halonitrobenzene such as 2-chloronitrobenzene or 2-bromonitrobenzene.

2) The thiosalicylic acid compound of Formula III is thiosalicylic acid or 5-methoxythiosalicylic acid.

3) In the first step of the method of preparing dibenzothiazepine compounds, a base such as potassium hydroxide is used.

4) The 2-nitro-2'-carboxydiphenylsulfide derivative of Formula IV is 2-nitro-2'-carboxydiphenylsulfide or 2-nitro-2'-carboxy-4'-methoxydiphenylsulfide.

5) In the reduction of the second step of the method of preparing a dibenzothiazepine compound, Pd—Pt/C catalyst is employed and ethyl acetate is employed as the solvent.

6) In the dehydration condensation step of the method of preparing a dibenzothiazepine, para-toluene sulfonic acid, or other such acids, are used.

A dibenzothiazepine compound represented by Formula I and of value as an intermediate compound for preparing pharmaceuticals can be easily produced at high yield with easy procedures according to the methods described herein.

In order that the invention disclosed herein may be more efficiently understood, examples are provided below. It should be understood that these examples are for illustrative purposes only and are not to be construed as limiting the invention in any manner.

EXAMPLES

Example 1

For Step-1

Thiosalicylic (20 g, 0.126 mol, 96.9%) and 2-chloronitrobenzene (24.6 g, 0.156 mol, 99.7%) were added to an appropriate vessel, followed by IPA (50 ml) and water (10 ml) at 20-25° C. The reactor was inerted (nitrogen), the suspension was heated to 30-35° C. and a solution of KOH aq (30.9 g, 0.273 mol, 49.51% w/w) was added, followed by a water wash (24.4 ml). The reaction mixture was heated to reflux and was maintained at this temperature for 6 hours. On completion of the reaction, the solution was cooled to 65° C. and water (50 ml) was added. The solution was held at 65° C. and c.HCl (20 g) was added, leading to precipitation of crude Nitro Acid. The suspension was re-heated to reflux and stirred at this temperature for 1 hour. The solution was then cooled to 25-30° C. After stirring for 30 min at 25-30° C., the suspension was filtered and the cake was washed with water (2×40 ml) and toluene (2×40 ml) and was left on the filter under vacuum for 1 hour to give 2-(2-nitrophenylsulfuryl)benzoic acid (31.1 g at 100% w/w, 90%).

Example 2

For Step-2

Nitro Acid (43.0 g, 145 mmol, 93%), Pd—Pt/C catalyst (8 g wet, 0.076% w/w, dry) and ethyl acetate (400 ml) were charged to an appropriate reactor at 20-25° C. Hydrogen was introduced to the vessel up to 5 barg. The reaction suspension was heated to 50° C. and the suspension was heated at 50° C. at 5 barg pressure of hydrogen for 5 hours. At the end of the reaction, the vessel contents were filtered. The ethyl acetate solution of Amino Acid was washed with water (120 ml).

Example 3

For Step-3

Para-Toluene sulphonic acid (41 mg, 0.2175 mmol) was added to the ethyl acetate solution obtained in Example 2, and approx. 50% of the ethyl acetate was removed by distillation. Xylene (320 ml) was added to the reactor and the distillation was continued until a batch temperature of 125° C. was reached. The reaction was then heated for 10 hours with azeotropic removal of water. The vessel contents were cooled to 55° C. and the resulting suspension was filtered. The cake was washed with methanol (120 ml), isolated and dried in vacuo to give 10,11-dihydrodibenzo[b,f][1,4]thiazepin-11-one (28.4 g, 86%).

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, and the like) cited in the present application is incorporated herein by reference in its entirety.

What is claimed is:

1. A method of preparing a dibenzothiazepine compound of Formula I:

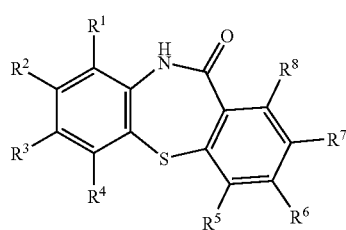

in which each of $R^1$, $R^2$, $R^3$, $R^4$, $R^5$, $R^6$, $R^7$, and $R^8$, independently, represents a hydrogen atom, an alkyl group, an alkoxy group, an alkylcarbonyl group, an aryl group, an aryloxy group, or an arylcarbonyl group, each group being optionally substituted, which comprises steps of:

reducing a 2-nitro-2'-carboxy-diphenylsulfide compound of Formula IV:

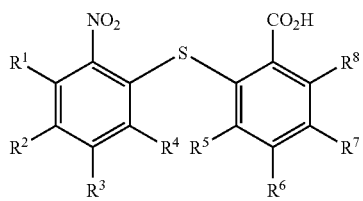

in which each of $R^1$, $R^2$, $R^3$, $R^4$, $R^5$, $R^6$, $R^7$ and $R^8$ is the same as defined above, in an aliphatic ester of an aliphatic alcohol having 1 to 6 carbon atoms and an aliphatic carboxylic acid having 1 to 6 carbon atoms to obtain the 2-amino-2'-carboxy-diphenylsulfide compound of Formula V:

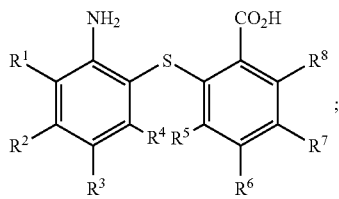

and subjecting the 2-amino-2'-carboxy-diphenylsulfide compound of Formula V to dehydration-condensation reaction in the presence of an acidic catalyst.

2. The method of claim 1, wherein the acidic catalyst is at least one compound selected from the group consisting of para-toluene sulphonic acid, benzene sulfuric acid, meth-ane sulfonic acid, sulfuric acid, and phosphoric acid.

3. The method of claim 1, wherein the aliphatic ester is at least one ester selected from the group consisting of methyl acetate, ethyl acetate, isopropyl acetate and n-butyl acetate.

4. The method of claim 1, wherein the reducing step is performed in the presence of at least one catalyst selected from the group consisting of Pd/C, Pt/C, and Pd-Pt/C.

5. The method of claim 1, wherein the following step is performed before the reducing step:

a step of reacting a nitrobenzene compound of Formula II:

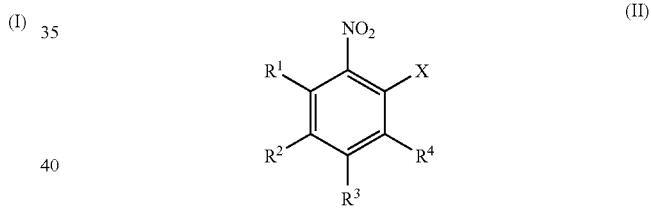

in which each of $R^1$, $R^2$, $R^3$, and $R^4$ is the same as defined above, with a thiosalicylic acid compound of Formula III:

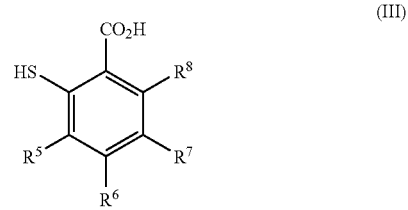

in which each of $R^5$, $R^6$, $R^7$ and $R^8$ is the same as defined above, in a mixture of an aliphatic alcohol having 1 to 6 carbon atoms and water to obtain the 2-nitro-2'-carboxy-diphenylsulfide compound of Formula IV.

6. The method of claim 5, wherein the mixture comprises the aliphatic alcohol and water in a volume ratio of 10/1 to 1/10 in terms of the former to the latter.

7. The method of claim 5, wherein the aliphatic alcohol is isopropyl alcohol.

8. The method of claim 5, wherein the reaction step is performed under reflux.

9. The method of claim 5, wherein the reaction is performed in the presence of a base.

10. A method of preparing a 2-amino-2'-carboxy-diphenylsulfide compound of Formula V:
in which each of $R^1$, $R^2$, $R^3$, $R^4$, $R^5$, $R^6$, $R^7$, and $R^8$, independently, represents a hydrogen atom, an alkyl group, an alkoxy group, an alkylcarbonyl group, an aryl group, an aryloxy group, or an arylcarbonyl group, each group being optionally substituted,
which comprises a step of reducing a 2-nitro-2'-carboxy-diphenylsulfide compound of Formula IV:

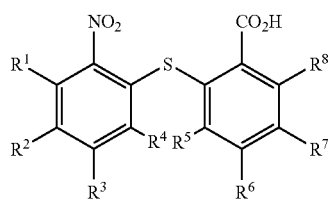

(IV)

in which each of $R^1, R^2, R^3, R^4, R^5, R^6, R^7$, and $R^8$ is the same as defined above, in an aliphatic ester of an aliphatic alcohol having 1 to 6 carbon atoms and an aliphatic carboxylic acid having 1 to 6 carbon atoms.

11. The method of claim 10, wherein the aliphatic ester is at least one ester selected from the group consisting of methyl acetate, ethyl acetate, isopropyl acetate and n-butyl acetate.

12. The method of claim 10, wherein the reducing step is performed in the presence of at least one catalyst selected from the group consisting of Pd/C, Pt/C, and Pd-Pt/C.

13. A method of preparing 2-nitro-2'-carboxy-diphenylsulfide compound of Formula IV:

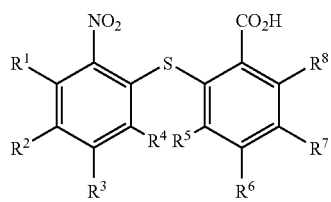

(IV)

in which each of $R^1$, $R^2$, $R^3$, $R^4$, $R^5$, $R^6$, $R^7$, and $R^8$, independently, represents a hydrogen atom, an alkyl group, an alkoxy group, an alkylcarbonyl group, an aryl group, an aryloxy group, or an arylcarbonyl group, each group being optionally substituted,
which comprises a step of reacting a nitrobenzene compound of Formula II:

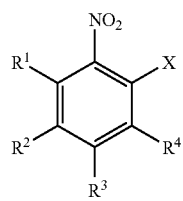

(II)

in which each of $R^1$, $R^2$, $R^3$, and $R^4$ is the same as defined above, with a thiosalicylic acid compound of Formula III:

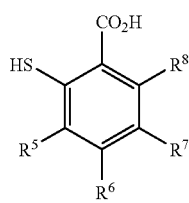

(III)

in which each of $R^5$, $R^6$, $R^7$ and $R^8$ is the same as defined above, in a mixture of an aliphatic alcohol having 1 to 6 carbon atoms and water.

14. The method of claim 13, wherein the mixture comprises the aliphatic alcohol and water in a volume ratio of 10/1 to 1/10 in terms of the former to the latter.

15. The method of claim 13, wherein the aliphatic alcohol is isopropyl alcohol.

16. The method of claim 13, wherein the reaction step is performed under reflux.

17. The method of claim 13, wherein the reaction is performed in the presence of a base.

* * * * *